United States Patent [19]

Ishii et al.

[11] 4,111,984

[45] * Sep. 5, 1978

[54] PROCESS FOR PRODUCING UNSATURATED ALDEHYDES, AND UNSATURATED FATTY ACIDS

[75] Inventors: Hiromichi Ishii; Hideo Matsuzawa; Masao Kobayashi, all of Ohtake; Kantaro Yamada, Yokohama, all of Japan

[73] Assignee: Mitsubishi Rayon Co., Ltd., Tokyo, Japan

[*] Notice: The portion of the term of this patent subsequent to Aug. 3, 1993, has been disclaimed.

[21] Appl. No.: 667,371

[22] Filed: Mar. 16, 1976

Related U.S. Application Data

[63] Continuation-in-part of Ser. No. 474,218, May 29, 1974, Pat. No. 3,972,920.

[30] Foreign Application Priority Data

| Jun. 11, 1973 | [JP] | Japan | 48-65563 |
| Aug. 28, 1973 | [JP] | Japan | 48-96345 |
| Dec. 18, 1973 | [JP] | Japan | 48-142118 |
| Dec. 26, 1973 | [JP] | Japan | 49-144000 |

[51] Int. Cl.$^2$ .................... C07C 51/24; C07C 51/32
[52] U.S. Cl. .................... 562/538; 252/443; 252/456; 252/464; 252/469; 252/470; 260/603 C; 260/604 R; 562/546
[58] Field of Search .......... 260/531 R, 533 N, 604 R, 260/603 C

[56] References Cited

U.S. PATENT DOCUMENTS

| 3,642,930 | 2/1972 | Grasselli et al. | 260/533 N |
| 3,993,680 | 11/1976 | Grasselli et al. | 260/533 N |
| 4,001,317 | 1/1977 | Grasselli et al. | 260/533 N |
| 4,065,507 | 12/1977 | Hardman et al. | 260/603 C |

FOREIGN PATENT DOCUMENTS

2,427,670  1/1975  Fed. Rep. of Germany ...... 260/531 R

*Primary Examiner*—Vivian Garner
*Attorney, Agent, or Firm*—Oblon, Fisher, Spivak, McClelland & Maier

[57] ABSTRACT

At least one compound from the group of unsaturated hydrocarbons of three to four carbon atoms and t-butyl alcohol is oxidized catalytically in the gas phase in the presence of molecular oxygen at 200°–450° C to produce the corresponding aldehyde or acid over a calcined catalyst of the formula $Mo_aSb_bBi_cFe_dNi_eSn_fX_gY_hO_i$ wherein X is at least one of potassium, rubidium or cesium, Y is at least one of cobalt, uranium, germanium, tungsten or titanium, $a$ to $h$ are atomic ratios wherein $a=12$, $b=0.2$ to 20, $c=0.2$ to 12, $d=0.2$ to 12, $e=0.2$ to 12, $f=0$ to 20, $g=0.01$ to 4 and $h=0$ to 6 and $i$ is a value determined by the oxidation state of the metal atoms in the catalyst. An embodiment of the calcined catalyst of the invention has the formula $Mo_aSb_bBi_cFe_dNi_eSn_fX_gY_hZ_jO_i$ wherein X and y are as defined above and Z is palladium and $a$ to $j$ are atomic ratios wherein $a=12$, $b=0.2$ to 20, $c=0.2$ to 12, $d=0.2$ to 12, $e=0.2$ to 12, $f=0$ to 20, $g=0.01$ to 4, $h=0.01$ to 3, $j=0.01$ to 3 and $i$ assumes a value determined by the oxidation states of the metal atoms in the catalyst.

6 Claims, No Drawings

PROCESS FOR PRODUCING UNSATURATED ALDEHYDES, AND UNSATURATED FATTY ACIDS

CROSS REFERENCE TO RELATED APPLICATIONS

This application is a continuation-in-part of application Ser. No. 474,218, filed May 29, 1974, now U.S. Pat. No. 3,972,920.

BACKGROUND OF THE INVENTION

1. Field of the Invention

This invention relates to a process for producing unsaturated aldehydes, or unsaturated fatty acids by catalytic oxidation of t-butyl alcohol, or unsaturated hydrocarbons containing 3 to 4 carbon atoms.

2. Description of the Prior Art

Heretofore, various processes have been known for the catalytic oxidation of propylene or isobutylene to the corresponding unsaturated aldehydes. For example Japanese Patent Publication No. 32049/72 discloses the oxidation of olefins over a catalyst comprising molybdenum, antimony, bismuth, iron, nickel and oxygen and a catalyst formed by the addition of tin to the basic catalyst. When propylene is catalytically oxidized with this catalyst, as much as 90 to 91% total selectivity of acrolein and acrylic acid can be obtained at propylene conversions of 95%. However, the amount of the by-products produced is comparatively large, namely, the total selectivity of carbon monoxide and carbon dioxide is as much as 6 to 8%. On the other hand, when isobutylene is oxidized over this catalyst, carbon monoxide and carbon dioxide by-products are produced in such significantly increased amounts that selectivity of methacrolein is decreased from an industrial standpoint, such favorable resuls as improvement in productivity and the removal of the heat of reaction are achieved by suppressing the formation of the gaseous by-products as much as possible. A process in which methacrolein is produced by the gas phase oxidation of t-butyl alcohol is disclosed by laid open Japanese Pat. No. 32814/73. The catalyst used in this process contains thallium, but the yield of methacrolein in a catalyst system not containing thallium is only about 40%.

Another prior art catalytic oxidation procedure is known as shown by Grasselli et al U.S. Pat. No. 3,642,930 in which an oxide catalyst containing molybdenum, iron, bismuth and an alkali metal is employed for the oxidative dehydrogenation of olefins to diene materials. In this type of reaction two hydrogen atoms are withdrawn from the olefin introducing a new site of unsaturation in the olefin. This is a completely different type of reaction, however, than the oxidative reaction of the present invention in which at least two of the hydrogen atoms on a methyl group in an olefin are extracted and replaced by at least on oxygen atom to form at least an aldehyde. If the oxidation reaction proceeds further, the correspondng carboxylic acid is produced. In fact, the Grasselli reference specifically indicates an awareness of the sensitivity of olefins to catalytic oxidation reactions by stating that even within the confines of a specific olefin oxydehydrogenation reaction, one catalyst may quite conspicuously not be able to perform as well as another even somewhat similar catalyst. An example of this unpredictability of olefin oxidation reactions is evident from the fact that while the bismuth, molybolenum, iron and nickel oxide catalyst of U.S. Pat. No. 3,424,631 is particularly effective as an oxydehydrogenation catalyst for the conversion of butene to butadiene, it is significantly less effective for the conversion of isoamylenes to isoprene. Accordingly, a need continues to exist for a method of catalytically oxidizing a $C_3$ or $C_4$ olefin or t-butylalcohol starting material to the corresponding unsaturated aldehyde or carboxylic acid in high yields and selectivity.

SUMMARY OF THE INVENTION

An object of the present invention is to provide a novel catalyst for producing methacrolein in high yield from isobutylene or t-butyl alcohol.

Another object of the present invention is to provide a method for the catalytic oxidation of isobutylene or t-butyl alcohol to methacrolein in high yield and selectivity.

Briefly, these objects and other objects of the invention as hereinafter will become more readily apparent can be attained by a process for oxidizing isobutylene or t-butyl alcohol catalytically in the gaseous phase over a catalyst having the formula:

$$Mo_a Sb_b Bi_c Fe_d Ni_e Sn_f X_g Y_h O_i$$

wherein X is at least one alkali metal selected from potassium, rubidium and cesium, Y is at least one metal selected from cobalt, uranium, germanium, tungsten, and titanium, $a$ to $h$ are atomic ratios wherein $a=12$, $b=0.2$ to 20, $c=0.2$ to 12, $d=0.2$ to 12, $e=0.2$ to 12, $f=0$ to 20, $g=0.01$ to 4, $h=0$ to 6 and $i$ is a value determined by the state of oxidation of the metal atom components of the catalyst. Acrolein can also be produced over the above described catalyst from propylene.

DETAILED DESCRIPTION OF THE PREFERRED EMBODIMENTS

The catalyst of the present invention can be prepared by any known method. A convenient source of molybdenum in the preparation of the catalyst is an oxide of the metal or any molybdenum compound convertible upon heating into an oxide. A preferred molybdenum compound is ammonium molybdate. Preferred sources for antimony and tin include the oxides, hydrated oxides and chlorides thereof. Preferred sources for bismuth, iron, nickel and the alkali metal include the oxides and compounds convertible upon heating into oxides such as nitrates, carbonates and hydroxides. The mixed metal oxide catalyst can also be supported on a carrier. Suitable carriers include silica, alumina and silicon carbide. The atomic ratio of each component in the catalyst can be varied within the ranges mentioned above. A particularly preferred set of ranges is $a=12$; $b=0.5$ to 20, $c=0.5$ to 6, $d=0.5$ to 6, $e=0.5$ to 6 and $g=0.01$ to 2. When tin is added to the catalyst, the strength of the catalyst is increased and the catalyst life is increased. The amount of tin added is, in terms of the atomic ratio, $f=0.5$ to 12 when $a$ is 12.

By the addition of palladium, cobalt, uranium, germanium, tungsten or titanium to the catalyst, the reaction temperature can be lowered and yield of methacrolein improved. Suitable sources of these metals include the oxides thereof and compounds convertible upon heating to the oxides thereof. The amount of these metals added is preferably, in terms of the atomic ratio, $h=0.01$ to 3 when $a$ is 12.

In another embodiment of the reaction of the present invention t-butyl alcohol or an unsaturated hydrocarbon of three to four carbon atoms is oxidized in the presence of molecular oxygen to the corresponding unsaturated aldehyde or acid over a catalyst of the formula:

$$Mo_aSb_bBi_cFe_dNi_eSn_fX_gY_hZ_jO_i$$

wherein X is at least one alkali metal selected from the group of potassium, rubidium and cesium, Y is at least one metal selected from the group of cobalt, uranium, germanium, tungsten and titanium, Z is palladium, $a$ to $j$ are atomic ratios wherein $a=12$, $b=0.2$ to 20, $c=0.2$ to 12, $d=0.2$ to 12, $e=0.2$ to 12, $f=0$ to 20, $g=0.01$ to 4, $h=0.01$ to 3 and $j=0.01$ to 3 and $i$ is determined by the oxidation state of the metal atoms in the catalyst.

In conducting the reaction of the present invention, starting materials such as isobutylene, or t-butyl alcohol are used, preferably diluted with at least one inert gas. Suitable inert gases, include nitrogen, steam and carbon dioxide. In particular, steam is preferably employed because it favorably influences the yield of product. Suitable oxygen sources for the catalytic oxidation reaction include air and air enriched in oxygen. The concentration of propylene, isobutylene or t-butyl alcohol can be varied within the range of 1 to 20 vol.%. The concentration of oxygen can also be varied within the range of 1 to 20 vol.%.

The reaction pressure is not critical and can range from normal pressure to several atmospheres. Suitable reaction temperatures range from 200° to 450° C, preferably from 250° C to 400° C. The contact time is preferably from 0.5 to 10 seconds. The reaction can be conducted either over a fixed bed or a fluidized bed catalyst.

Having now generally described the invention, a further understanding can be obtained by reference to certain specific examples which are provided herein for purposes of illustration only and are not intended to be limiting unless otherwise specified. In the examples the term "part" signifies "part by weight", and the yield is calculated by the following equation:

$$Yield = \frac{\text{Title product (meth) acrolein or (meth) acrylic acid moles}}{\text{Starting material charged (moles)}} \times 100$$

EXAMPLE 1

In 200 parts of water were suspended 27.6 parts of a fine powder of antimony pentoxide and a solution of 42.5 parts of ammonium molybdate dissolved in 200 parts of water was added thereto. Thereafter, a solution of 1.0 part of potassium nitrate dissolved in 10 parts of water, a solution of 48.5 parts of bismuth nitrate dissolved in 50 parts of 10% nitric acid and a solution of 16.4 parts of ferric nitrate and 5.9 parts of nickel nitrate dissolved in 100 parts of water were added in this order to the mixture. Finally, 45 parts of silica were added as a carrier in the form of silica sol. The slurry obtained was evaporated to dryness. The residue obtained was dried at 120° C, pelletted, and thereafter calcined at 500° C for 6 hours. The catalyst was packed in a reaction tube, heated to 305° C in an air bath, and a mixed feed gas containing 6% propylene, 12% oxygen, 47% nitrogen and 35% steam (all in mole %) was passed therethrough at a contact time of 3.6 seconds. The gas formed was analyzed by gas chromatography resulting in a total yield of acrolein and acrylic acid of 89.7%.

EXAMPLE 2

By the use of the catalyst of Example 1, a mixed feed gas containing 5% t-butyl alcohol, 12% oxygen, 48% nitrogen and 35% steam (all in mole %) was introduced into the catalyst layer maintained at 385° C and passed therethrough at a contact time of 3.6 seconds. An analysis of the gaseous product by gas chromatography indicated a total yield of methacrolein and methacrylic acid of 78.0%.

EXAMPLE 3

By using a catalyst having the same composition as that of Example 1, except that 1.5 parts of rubidium nitrate were added to the catalyst ingredients, the reaction was conducted under the same conditions of Example 1 except that the bath temperature was maintained at 310° C resulting in a total yield of acrolein and acrylic acid of 92.0%.

EXAMPLE 4

By using a catalyst having the same composition as described in Example 1, except that 0.78 parts of cesium nitrate was added to the catalyst ingredients, the reaction was conducted under the same conditions except that the bath temperature was maintained at 310° C whereby a total yield of acrolein and acrylic acid of 91.7% was obtained.

EXAMPLE 5

Using the catalyst of Example 4, a mixed feed gas containing 6% isobutylene, 12% oxygen, 47% nitrogen and 35% steam (all in mole %) was passed over the catalyst at a contact time of 3.6 seconds. The total yield of methacrolein and methacrylic acid was found to be 75.8%.

EXAMPLE 6

The reaction of Example 4 was repeated using the same catalyst under the conditions of Example 2 except that the bath temperature was maintained at 380° C. The total yield of methacrolein and methacrylic acid was found to be 81.5%.

EXAMPLE 7

In 200 parts of water were suspended 27.6 parts of finely powdered antimony pentoxide and a solution of 42.5 parts of ammonium molybdate dissolved in 200 parts of potassium nitrate dissolved in 10 parts of water, a solution of 29.1 parts of bismuth nitrate dissolved in 50 parts of 10% nitric acid and a solution of 8.2 parts of ferric nitrate and 11.8 parts of nickel nitrate dissolved in 100 parts of water were added in this order to the mixture. Thereafter, a solution of 14.4 parts of stannous chloride dissolved in 50 parts of 10% nitric acid was added to the mixture and finally 45 parts of silica sol were added thereto. The slurry obtained was evaporated to dryness. The residue obtained was dried at 120° C and thereafter calcined at 500° C for 6 hours. By using this catalyst and maintaining the bath temperature of 300° C, the reaction was performed under otherwise the same conditions as in Example 1. As a result, the total yield of acrolein and acrylic acid was found to be 91.0%.

EXAMPLE 8

The reaction of Example 7 was repeated using the same catalyst under the reaction conditions of Example 5 except that the bath temperature was maintained at 375° C. As a result, the total yield of methacrolein and methacrylic acid was found to be 77.0%.

EXAMPLE 9

The reaction of Example 7 was repeated using the same catalyst under the conditions of Example 2 except that the bath temperature was maintained at 375° C. The total yield of methacrolein and methacrylic acid was found to be 79.0%.

EXAMPLE 10

In 200 parts of water were suspended 27.6 parts of finely powdered antimony pentoxide and a solution of 42.5 parts of ammonium molybdate dissolved in 200 parts of water was added to this suspension. Then, a solution of 1.0 part of potassium nitrate and 0.78 parts of cesium nitrate dissolved in 20 parts of water, a solution of 48.5 parts of bismuth nitrate dissolved in 50 parts of 10% nitric acid, a solution of 16.4 parts of ferric nitrate, 5.9 parts of nickel nitrate and 11.6 parts of cobalt nitrate dissolved in 100 parts of water and a solution of 0.92 parts of palladium nitrate dissolved in 20 parts of water were added in this order to the mixture. To the mixture was added 45 parts of silica as a carrier in the form of silica sol. The slurry obtained was evaporated to dryness and the residue was dried at 120° C, pelleted and calcined at 500° C under an air stream for 6 hours to yield the catalyst.

EXAMPLE 11

A catalyst was prepared in the same manner described in Example 10 except that 1.05 parts of germanium oxide were added instead of cesium nitrate, cobalt nitrate and palladium nitrate to the catalyst ingredients.

EXAMPLE 12

A catalyst was prepared in the same manner described in Example 10 except that 2.7 parts of ammonium tungstate were added instead of cesium nitrate, palladium nitrate and cobalt nitrate to the catalyst ingredients.

EXAMPLE 13

A catalyst was prepared in the same manner described in Example 10 except that 3.2 parts of titanium oxide were added instead of cesium nitrate, palladium nitrate and cobalt nitrate to the catalyst ingredients.

EXAMPLE 14

A catalyst was prepared in the same manner described in Example 10 except that 10.0 parts of uranyl nitrate were added instead of cesium nitrate, palladium nitrate and cobalt nitrate to the catalyst ingredients.

EXAMPLE 15

In 200 parts of water were suspended 27.6 parts of finely powdered antimony pentoxide and a solution of 42.5 parts of ammonium molybdate dissolved in 200 parts of water was added to the suspension. Thereafter, a solution of 2.0 parts of potassium nitrate dissolved in 10 parts of water, a solution of 29.1 parts of bismuth nitrate dissolved in 50 parts of 10% nitric acid, a solution of 8.2 parts of ferric nitrate and 11.8 parts of nickel nitrate dissolved in 100 parts of water, and a solution of 5.0 parts of uranyl nitrate dissolved in 20 parts of water were added in this order to the mixture, followed by addition of a solution of 14.4 parts of stannous chloride dissolved in 50 parts of 10% nitric acid and finally 45 parts of silica sol. The slurry obtained was evaporated to dryness and the resulting residue was dried at 120° C, pelleted and calcined at 500° C for 6 hours. The product was used as a catalyst.

EXAMPLE 16

A catalyst was prepared in the same manner described in Example 15 except that 5.8 parts of cobalt nitrate were added instead of uranyl nitrate.

EXAMPLE 17

A catalyst was prepared in the same manner described in Example 15 except that 0.46 parts of palladium nitrate and 1.6 parts of titanium oxide were further added to the composition.

Each catalyst prepared in Examples 10 to 17 was used in an oxidation reaction wherein a mixed feed gas containing 5% t-butyl alcohol, 12% oxygen, 48% nitrogen and 35% steam (all in mole %) was introduced into each catalyst layer maintained at the temperatures indicated below at a contact time of 3.6 seconds. The gaseous products formed were analyzed and the results obtained are shown in Table 1.

TABLE I

| Example Number | Catalyst Elements | Reaction temperature (° C) | Yield of methacrolein and methacrylic acid (%) |
|---|---|---|---|
| 10 | Mo—Sb—Bi—Fe—Ni—K—Cs—Pd—Co | 330 | 84.0 |
| 11 | Mo—Sb—Bi—Fe—Ni—K—Ge | 345 | 82.5 |
| 12 | Mo—Sb—Bi—Fe—Ni—K—W | 360 | 81.0 |
| 13 | Mo—Sb—Bi—Fe—Ni—K—Ti | 355 | 82.2 |
| 14 | Mo—Sb—Bi—Fe—Ni—K—U | 365 | 81.5 |
| 15 | Mo—Sb—Bi—Fe—Ni—Sn—K—U | 350 | 82.3 |
| 16 | Mo—Sb—Bi Fe—Ni—Sn—K—Co | 355 | 83.5 |
| 17 | Mo—Sb—Bi—Fe—Ni—Sn—K—U—Pd—Ti | 340 | 83.1 |

Having now fully described the invention, it will be apparent to one of ordinary skill in the art that many changes and modifications can be made thereto without departing from the spirit or scope of the invention as set forth herein.

What is claimed as new and intended to be secured by Letters Patent is:

1. In a process for the gas phase catalytic oxidation of t-butyl alcohol in the presence of molecular oxygen at 200° C to 450° C to produce mixtures of the corresponding aldehyde and acid, the improvement comprising: oxidizing said compound over a calcined catalyst consisting essentially of $Mo_a Sb_b Bi_c Fe_d Ni_e Sn_f X_g Y_h O_i$ wherein X is at least one alkali metal selected from the group consisting of potassium, rubidium and cesium, Y is at least one metal selected from the group consisting of cobalt, uranium, germanium, tungsten and titanium, and $a$ to $h$ are atomic ratios wherein $a = 12$, $b = 0.2$ to 20, $c = 0.2$ to 12, $d = 0.2$ to 12, $e = 0.2$ to 12, $f = 0$ to 20, $g = 0.01$ to 4 and $h = 0$ to 6, and $i$ is determined according to the oxidation states of the metal atoms in the catalyst.

2. The process of claim 1, wherein the component X is potassium.

3. The process of claim 1, wherein the component X is cesium.

4. The process of claim 1, wherein the component X is potassium and cesium.

5. The process of claim 1, wherein the atomic ratios $a$ to $h$ of the catalyst are defined as: $a=12$, $b=0.5$ to 20, $c=0.5$ to 6, $d=0.5$ to 6, $e=0.5$ to 6, $f=0$ to 20, $g=0.01$ to 2 and $h=0.01$ to 3.

6. In a process for the gas phase catalytic oxidation of at least one compound selected from the group consisting of olefinic hydrocarbons of 3 to 4 carbon atoms and t-butyl alcohol in the presence of molecular oxygen at 200° to 450° C to produce mixtures of the corrsponding aldehyde and acid, the improvement comprising: oxidizing said compound over a calcined catalyst consisting essentially of $Mo_aSb_bBi_cFe_dNi_eSn_fX_gY_hZ_jO_i$ wherein X is at least one alkali metal selected from the group consisting of potassium, rubidium and cesium; Y is at least one metal selected from the group consisting of cobalt, uranium, geranium, tungsten and titanium; Z is palladium; and $a$ to $j$ are atomic ratios wherein $a=12$, $b=0.2$ to 20, $c=0.2$ to 12, $d=0.2$ to 12, $e=0.2$ to 12, $f=0$ to 20, $g=0.01$ to 4, $h=0.01$ to 3, $j=0.01$ to 3 and $i$ is determined according to the oxidation states of the metal atoms in the catalyst.

* * * * *